United States Patent
Ericson et al.

(10) Patent No.: US 6,790,603 B2
(45) Date of Patent: Sep. 14, 2004

(54) COMPOSITIONS FOR THE STORAGE OF PLATELETS

(75) Inventors: Daniel G. Ericson, Rochester, MN (US); John St. Cyr, Coon Rapids, MN (US)

(73) Assignee: Bioenergy, Inc., Ham Lake, MN (US)

( * ) Notice: Subject to any disclaimer, the term of this patent is extended or adjusted under 35 U.S.C. 154(b) by 100 days.

(21) Appl. No.: 09/746,553

(22) Filed: Dec. 21, 2000

(65) Prior Publication Data

US 2002/0034722 A1 Mar. 21, 2002

Related U.S. Application Data

(60) Provisional application No. 60/171,278, filed on Dec. 21, 1999, and provisional application No. 60/189,285, filed on Mar. 14, 2000.

(51) Int. Cl.[7] .................................................. C12N 5/00
(52) U.S. Cl. .............................. 435/2; 435/1.1; 435/1.3; 436/18
(58) Field of Search .............................. 435/2, 1.1, 1.3; 436/18

(56) References Cited

U.S. PATENT DOCUMENTS

| | | | |
|---|---|---|---|
| 4,447,415 A | 5/1984 | Rock et al. | 424/101 |
| 4,572,899 A | 2/1986 | Walker et al. | 436/18 |
| 4,828,976 A | 5/1989 | Murphy | 435/2 |
| 5,213,814 A | 5/1993 | Goodrich, Jr. et al. | 424/532 |
| 5,231,025 A | 7/1993 | Gralnick | 435/240.27 |
| 5,418,130 A * | 5/1995 | Platz et al. | |
| 5,470,738 A | 11/1995 | Frelinger, III et al. | 435/240.27 |
| 6,159,942 A | 12/2000 | St. Cyr et al. | 514/23 |

OTHER PUBLICATIONS

Dawson, R.B., et al., "Blood Preservation 33. Phosphate Enhancement of Ribose Maintenance of 2,3–DPG and ATP", *Transfusion, 21* (2), pp. 215–218, (Mar.–Apr. 1981).

Dawson, R.B., et al., "Blood Preservation 50: Red Cell 2,3–DPG Maintenance in CPD–Adenine Stored Blood by Several Mechanisms", *The Red Cell: Fifth Annual Arbor Conference,* pp 643–660, (1981).

Mitchell, W.M., et al., "Comparative Aspects of Sugar Penetration into Blood Platelets", *Biochem. Physiol., vol. 32,* 813–815, (1970).

Djerassi, I., et al., "A Method for Preservation of Viable Platelets: Combined Effects of Sugars and Dimethylsulfoxide", *Blood, 22* (6) , pp. 703–717, (1963).

* cited by examiner

Primary Examiner—Leon B. Lankford, Jr.
(74) *Attorney, Agent, or Firm*—Kathleen R. Terry

(57) ABSTRACT

Blood platelets stored in an isotonic, balanced salt solution under standard storage conditions retain function after ten days of storage when micormolar or nanomolar amounts of pentose are added to the solution. The preferred pentoses are D-Ribose, xylulose-5-phosphate and the pentose-related alcohol xylitol.

8 Claims, 9 Drawing Sheets

Platelets - SEM

Basal Platelets     Activated Platelets

Basal P-selectin expression 3 day storage at room temperature, 153 nM D-Ribose

P-Selectin – 10nM Thrombin

3 day storage at room temperature, 153 nM D-Ribose

COMPOSITIONS FOR THE STORAGE OF PLATELETS

RELATED APPLICATIONS

This application claims benefit under 35 U.S.C. of U.S. Provisional Application No. 60/171,278, filed Dec. 21, 1999 and U.S. Provisional Application No. 60/189,285, filed Mar. 14, 2000.

BACKGROUND OF THE INVENTION

About 12.6 million units (including approximately 643,000 autologous donations) of whole blood are donated in the United States each year by approximately eight million volunteer blood donors. These units are transfused to about four million patients per year. Typically, each donated unit of blood, referred to as whole blood, may be separated into multiple components, such red blood cells, plasma, clotting factors, gamma globulin and platelets. The need for blood is great: on any given day, approximately 32,000 units of red blood cells are needed. Accident victims, people undergoing surgery and patients receiving treatment for leukemia, cancer or other diseases, such as sickle cell disease and thalassemia, all utilize blood.

Because patients seldom require all of the components of whole blood, it is the usual practice in blood banks to separate the blood into components and transfuse only that portion needed by the patient for a specific condition or disease. This treatment, referred to as "blood component therapy," allows several patients to benefit from one unit of blood.

Whole blood is a living tissue that circulates through the heart, arteries, veins and capillaries, carrying nourishment, electrolytes, antibodies, heat and oxygen to the body tissues. Whole blood is comprised of red blood cells, white blood cells and platelets suspended in a proteinaceous fluid termed blood plasma. If blood is treated to prevent clotting and permitted to stand in a container, red blood cells will settle to the bottom of the container; the plasma will remain on top and the white blood cells will form a layer on top of the red blood cells. A centrifuge is commonly used to hasten this separation. The platelet-rich plasma is then removed and placed into a sterile bag for further processing to separate, for example platelets, clotting factors, albumin, immunoglobulin and the like.

Red blood cells contain hemoglobin, a complex iron-containing protein that carries oxygen throughout the body and gives blood its red color. The percentage of blood volume that is composed of red blood cells is called the "hematocrit." The average hematocrit is and adult male is 47%. There are about one billion red blood cells in two or three drops of blood, and, for every 600 red blood cells, there are about 40 platelets and one white blood cell. Manufactured in the bone marrow, red blood cells are continuously being produced and broken down and removed by the spleen after an average 120 days in the circulatory system. Red blood cells are prepared from whole blood by removing the plasma and can raise the patient's hematocrit while minimizing and increase in blood volume, which is especially important to such patients as those with congestive heart failure. Patients benefiting most from transfusions of red blood cells include those with chronic anemia from disorders such as kidney failure, malignancies, gastrointestinal bleeding and acute blood loss as from trauma or surgery. Red blood cells may be treated and frozen for extended storage up to ten years.

Storage of these components varies. Improvements in cell preservation solutions over the last 15 years have increased the refrigerated shelf life of whole blood or red blood cells from 21 to 42 days. Plasma can be frozen and kept much longer. The isolated proteins such as clotting factors may be freeze dried for indefinite shelf life.

Platelets or thrombocytes are very small cellular components of blood that are programmed to aggregate in various conditions. Platelets are produced in the bone marrow and survive in the circulatory system for an average of nine or ten days before being removed from the body by the spleen. Platelets are vital to life, because they help prevent massive blood loss from trauma and the blood vessel leakage that occurs during normal daily activity.

Platelet transfusions are an integral part of the support of patients at risk of bleeding. Platelets used for transfusion can come from two sources: platelet concentrates derived from units of whole blood, termed random donor platelet concentrates, or apheresis platelets obtained from a single donor by plateletpheresis, a technique of continuous separation of platelets from a donor, with simultaneous reinfusion of blood minus platelets back into the donor. A unit of platelets is defined as the concentration of platelets separated from a single unit of whole blood and suspended in a small amount of plasma. The accepted unit contains no fewer than $5.5 \times 10^{10}$ platelets suspended in 40–70 ml of plasma. The recommended dosage of platelets is one unit per 10 kilograms body weight. This dosing schedule can be used for infants, children or adults to yield an expected increment in platelet count of 5,000–10,000 per microliter per unit of platelets transfused. The smaller the patient, the larger the relative dose. Thus an infant or small child may require an increase to 25,000 to 50,000 per unit of platelets.

Whatever the mode of collection or use, platelet storage poses problems that are not found with the storage of whole blood or other components. It is noted above that whole blood, red and white cells may be stored at 4° C. for weeks. Platelets, which are programmed to aggregate and must be able to aggregate as part of their function, will aggregate in cold storage and when allowed to settle. Therefore, the standard means of storage of platelets is at room temperature, approximately 20 to 24° C., with gentle agitation. Even under these conditions, platelets lose function by five days.

An additional problem is bacterial contamination. While blood is drawn under the most stringent aseptic techniques, invariably a tiny number of bacteria may enter the collection bag. Additionally, white blood cells may have scavenged bacteria. If these cells should rupture, bacteria may be released. Reported organisms include *Staphylococcus epidermidis, Staphylococcus aureus*, bacillus sp., micrococcus sp., streptococcus sp., klebsiella sp. and Salmonella sp. The gold standard for detection of contamination is a negative Petri culture at two weeks. A reported prevalence of contamination of whole blood for transfusion is 48.5 per 100,000. The situation for platelets is worse: platelet bacterial contamination is ten times greater than for blood. It is thought that this higher prevalence is due to the fact that platelets are stored at room temperature, which favors bacterial growth. The United States FDA reports 37 deaths since 1996 due to contaminated platelets, while the incidence in France is about four deaths per year.

A need remains to provide compositions that will increase the survival time of platelets and reduce bacterial contamination.

SUMMARY OF THE INVENTION

Platelets stored under previously known conditions lose function by undergoing spontaneous activation so that by five days only about 5% of the platelets are functional. This invention provides pentose to be added to stored platelets in concentrations ranging from 50 nM to 15 µM, more preferably from 100 nM to 5 µM. Such treated platelets retain normal function for as long as five days and show significant function at ten days of storage. An unexpected and additional advantage of pentose addition is the inhibition of bacterial growth.

Platelet function is measured by (1) internal protein expression on the cell membrane in response to challenge with an activation-inducing agonist; (2) ability to aggregate when challenged by an agonist; and (3) adenosine triphosphate secretion. Internal protein expression may be measured by conjugation of a molecule with a fluorescent dye, followed by sorting in a fluorescent cell sorter. In general, it is preferable to use two monoclonal antibodies, one that binds a cell surface molecule expressed and a second that binds a cell surface molecule that is expressed only after activation. Each monoclonal antibody is conjugated to a different colored dye, that can be distinguished by spectrofluorometry. In the preferred embodiment, the normally expressed cell surface molecule is GPIIbIIIa; the cell surface molecule expressed after activation is P-selectin. It is well know in the art to make monoclonal antibodies to proteins. U.S. Pat. No. 5,470,738, issued in 1995 to Freilich et al, is one example of a method of making monoclonal antibodies to GPIIIa. Another anti-platelet monoclonal antibody is that to GP IV, as disclosed by U.S. Pat. No. 5,231,025, issued in 1993 to Gralnisch. However, it is most convenient to purchase antibodies commercially from such companies as Becton-Dickinson (Philadelphia).

A basal measurement of spontaneous activation is obtained and the cells are then challenged with an agonist. The difference between cells challenged to activate minus the basal measurement is a measure of cell function. In the preferred embodiment, the agonist is 10 nM thrombin.

Another parameter of platelet function is the ability to aggregate when challenged by an agonist. The platelet suspension is dense and milky white. Aggregation and subsequent settling of the aggregates can be estimated visually, or measured with a densitometer.

Yet another measure of platelet function is the secretion of ATP. Platelets that are able to function well are able to secrete ATP while cells that have already been activated or have lost function in other ways cannot secrete ATP.

For purposes of describing this invention, the following terms have these meanings:

Agonist means any ligand that will bind to a cell surface protein of a platelet and cause activation of platelet function. Agonists include thrombin, epinephrine, ADP and collagen.

Pentose means a five carbon sugar which is D-Ribose or xylulose or a five-carbon precursor of ribose. The pentose related alcohol xylitol is also included in the definition of pentose.

Standard platelet storage conditions means suspension at a concentration of about $10 \times 10^5$ to $10 \times 10^{10}$ platelets per milliliter in a balanced, isotonic salt solution with an initial pH of at least 7, agitated or rotated gently, in a gas permeable storage bag, kept at room temperature.

DETAILED DESCRIPTION OF THE INVENTION

Figure 1:
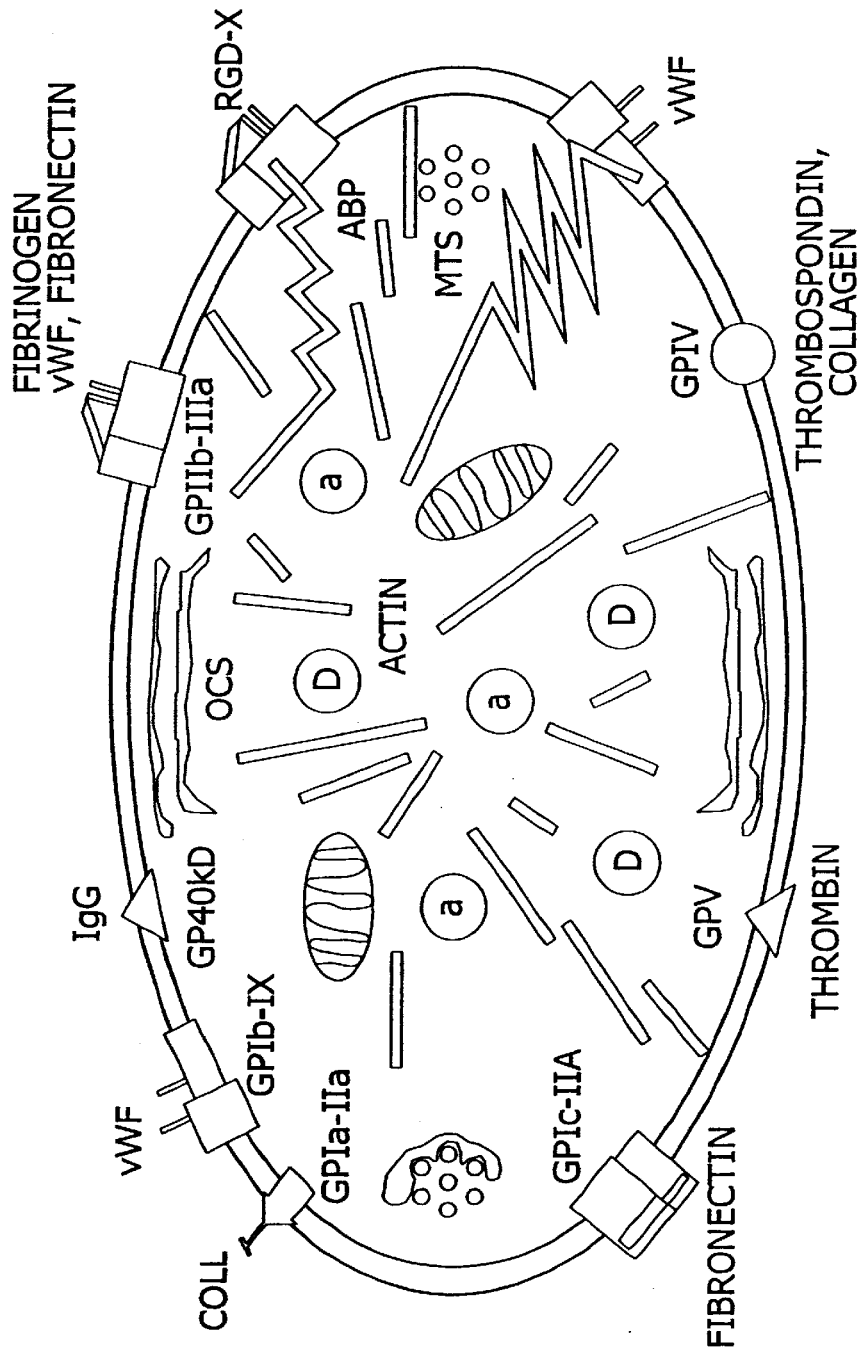
FIG. 1 is a schematic representation of platelet morphology.
Figure 2:
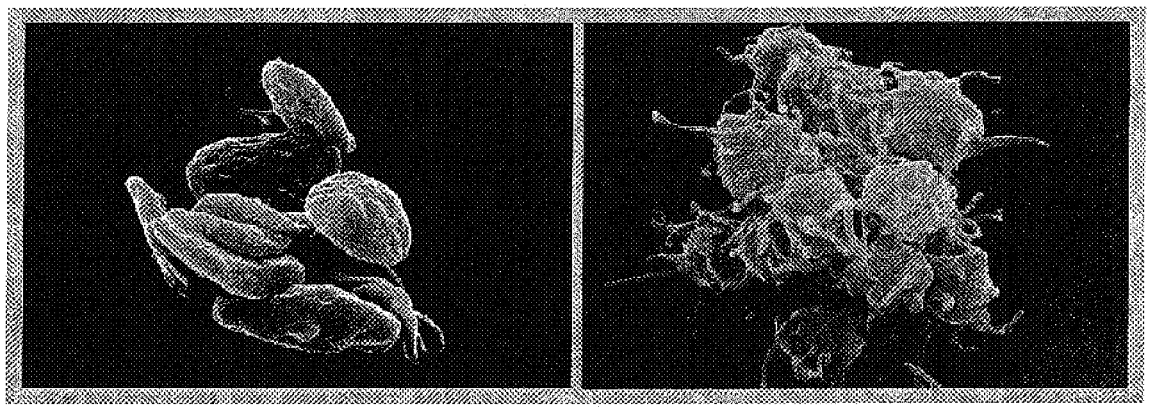
FIG. 2 is a scanning electron micrograph of platelets before and after activation.
Figure 3:
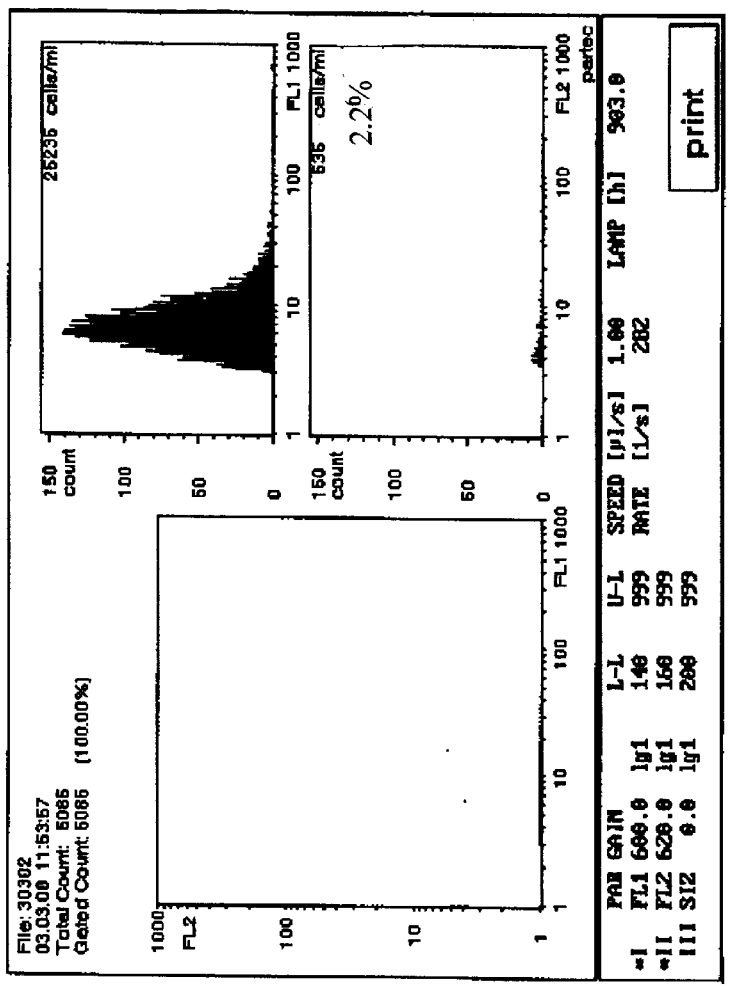
FIG. 3 shows basal P-selectin expression two hours after platelet collection (a) total platelets and (b) activated platelets.
Figure 4:
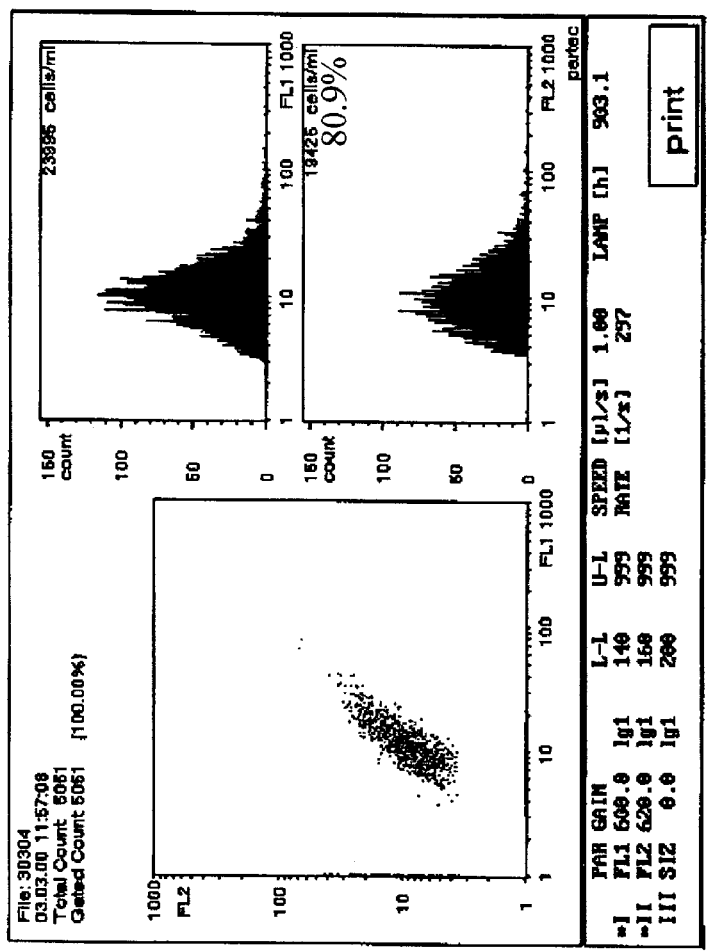
FIG. 4 shows basal selectin expression two hours after platelet collection (a) total platelets and (b) platelets activated with thrombin.

Platelets are enucleated cell fragments, pinched off from large bone marrow cells called megakaryocytes. Since they are enucleated, they have no mechanisms for renewal of expended proteins. Thus, once they are activated or have lost function, they remain nonfunctional. Although unable to synthesize protein for cell renewal, platelets contain more glycogen per unit cell mass than almost any other cell. As shown in FIG. 1, platelets also contain mitochondria, the organelle that carries out oxidative phosphorylation, which results in the synthesis of ATP. The storage container must be gas permeable, so that oxidative phosphorylation is favored over glycolysis, which results in the production of lactate and a klowering of pH. In addition, platelets have dense granules containing adenosine triphosphate. Thus, platelets are well equipped with energy and energy-producing substrates and the organelles necessary to carry out their function. FIG. 1 also illustrates some of the many cell surface receptors that play a role in regulating platelet function, and some of the internal proteins that are expressed on the cell surface following activation. Some particularly useful agonists for inducing activation experimentally are thrombin, epinephrine, ADP and collagen, although others are also usable in this invention. Likewise, any of the cell surface receptors can be used to estimate total number of platelets although GPIIbIIIa receptor is a convenient marker. Likewise, any internal protein that is displayed (expressed) on the platelet surface after agonist activation may be used to estimate the percentage of cells activated, although P-selectin is particularly useful. Activation causes morphological changes as seen in FIG. 2.

P-selectin is an internal protein that is exposed on the surface of the platelet after activation. Once activated, platelets cannot be activated again, that is, they are nonfunctional. Platelets which have aggregated are likewise nonfunctional. Measurement of P-selectin before and after activation with thrombin provides a measure of the ability of the platelets to be activated.

EXAMPLE 1

Assay for P-selectin Expression

P-selectin expression in response to a challenge of 10 nM thrombin is a highly accurate and quantitative method to assess platelet function using flow cytometry techniques. A monoclonal antibody to the platelet GPIIbIIIa receptor (Becton-Dickinson) is conjugated with green fluorescence, marking all platelets with a green detection. A red PE-conjugated monoclonal antibody (Becton-Dickinson) is added that stains only platelets that are activated and express P-selectin on the membrane of the platelet (resting, unactivated platelets do not have P-selectin expressed on their surfaces and thus accessible to the antibody). About 10,000 to 25,000 platelets are counted and measured for P-selectin expression and the % positive cells are defined as activated platelets that express P-selectin. Platelets that are activated are not capable of being activated a second time; that is, they are essentially nonfunctional.

EXAMPLE 2

Determination of the Concentration of Ribose for Storage of Platelets.

It was proposed years ago by Dawson (Transfusion 21:215–218. (1981)) that ribose at the concentration of 15 mM is beneficial to stored whole blood. It was assumed that ribose functioned by raising the energy levels of the cells, as discussed at length in U.S. Pat. No. 6,159,942. Subjects given ribose in that patent tolerated ingestion of 30 grams of ribose each day, with no ill effects. However, it should be noted that the platelet storage milieu is an austere environment, lacking the homeostatic and buffering mechanisms of the kidneys, lungs and livers of an intact organism. Various concentrations of D-Ribose were tested to determine the optimum level for platelet storage. The 15 mM as used by Dawson, used for whole blood storage, was the starting point, but that level of D-Ribose resulted in high lactate production with concomitant low pH. A drop in pH below about 6 is toxic to platelets so lower concentrations were tested. Platelet concentrate bags were obtained from a local transfusion center within two hours of collection from the donor. The platelets were either supplemented with the D-Ribose cocktail directly into the bag or the platelets were divided into a series of 10 tubes into each of which two ml of platelets were added. Platelet function was assessed by ATP secretion, platelet aggregation, P-selectin expression, platelet count and pH. Platelet function was measured every 24 hours. The bags and tubes were placed on a rotating wheel at room temperature for the duration of the experiment.

For the concentration test, platelets were stored for five days in standard platelet storage solution at room temperature and gentle agitation with or without various levels of ribose. At five days the P-selectin expression test was performed. As can be seen in Table I, 1.5 µM to 150 nM ribose was optimum for retention of activity.

TABLE I

D-Ribose Effect on Five Day Stored Platelets

| Sample | P-Selectin Expression | % Positive | Difference (% capable of being activated) |
| --- | --- | --- | --- |
| 0 Control | 15390 | 37.7 | |
| 0 Control + Thrombin | 15315 | 42.5 | 4.8 |
| 1.5 mM | 21605 | 40.4 | |
| 1.5 mM + Thrombin | 32400 | 60.0 | 34.4 |
| 15 µM | 3275 | 6.1 | |
| 15 µM + thrombin | 34960 | 64.4 | 58.3 |
| 150 nM | 2465 | 5.1 | |
| 150 nM + thrombin | 41480 | 65.7 | 60.6 |
| 150 pM | 11260 | 31.7 | |

TABLE I-continued

D-Ribose Effect on Five Day Stored Platelets

| Sample | P-Selectin Expression | % Positive | Difference (% capable of being activated) |
| --- | --- | --- | --- |
| 150 pM + thrombin | 15475 | 42.6 | 10.9 |

Platelets stored for five days without ribose were essentially nonfunctional as determined by the P-selectin expression test with thrombin challenge. 1.5 mM and 150 nM D-Ribose allowed the platelets to retain about 60% P-selectin expression activity, while 150 pM D-Ribose was ineffective in preserving function.

In summary, the flow cytometry data indicate that D-Ribose prevents platelets from aging during storage, and the response to agonist challenge does not decrease with time under these conditions. Simply, put the platelets are as active on day five as they were on day one if treated with D-Ribose.

4. P-selectin Expression in Platelets Stored for Three Days

Platelets were suspended in standard platelet storage cocktail and handled as above. U.S. Pat. No. 4,828,976 issued in 1989 to Murphy and U.S. Pat. No. 4,447,415 issued in 1984 to Rock, disclose several commonly used balanced salt solutions useful in this invention. Any solution may be used, provided it is isotonic (between about 310 and 140 mOsm), has a pH of at least 7.0 and contains magnesium ion. Representative cocktails are:

TABLE II

Typical plasma storage balanced salt solutions

| Ingredient | Applicant | Murphy | Rock |
| --- | --- | --- | --- |
| Citrate | 3.8% | 13–20 mM | 11.8 |
| Potassium | 3.6–4.8 mEq/liter | 2.5–5.5 mM | 2.4 |
| Sodium | 135–145 mEq/liter | 160–215 mM | 166 |
| Calcium | 2.0 | 2.5 | 1.8 |
| Magnesium | 1.7–2.1 mM | 0.25–1 mM | 1.2 |
| Bicarbonate | to adjust pH to 7.4 | 20–50 mM | to adjust pH to 7.4 |
| Glucose | 0 to millimolar | 0 | 22 |
| D-Ribose | 50 nM to 1.5 µM | 0 | 0 |

As can be noted from the table, the solute composition of these three platelet storage solutions is quite similar. Any of the above or others may be used in this invention, provided that magnesium is a component and the solution is isotonic and the pH is at least 7. Plasma may also be used as the solution to which ribose is added. The metal salts are typically chloride, phosphate, carbonate, bicarbonate or sulfate salts. Citrate is generally present because of carry-over from the blood collection, where it is present as an anticoagulant.

Platelets were tested for P-selectin expression to give a basal value. As is shown in FIG. 1, 2.2% of the platelets have already been activated at two hours. When activated by the addition of 10 nM thrombin, 80.9% of the cells are capable of activation as shown in FIG. 2.

Figure 5:
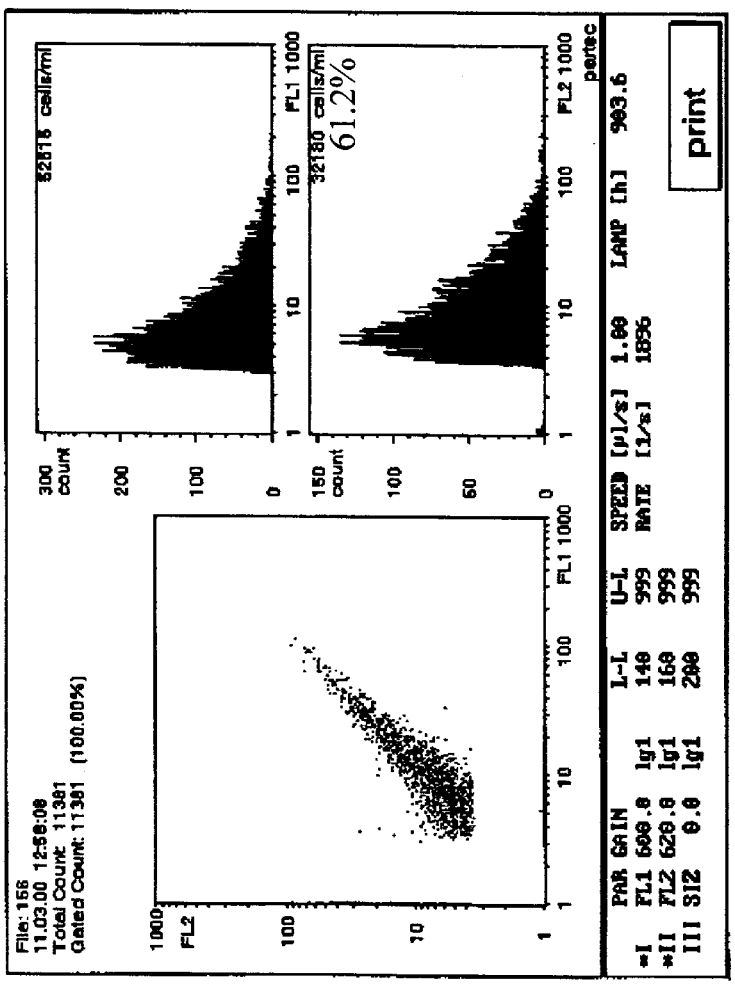
FIG. 5 shows platelets stored for three days without pentose (a) total platelets and (b) activated platelets.
Figure 6:
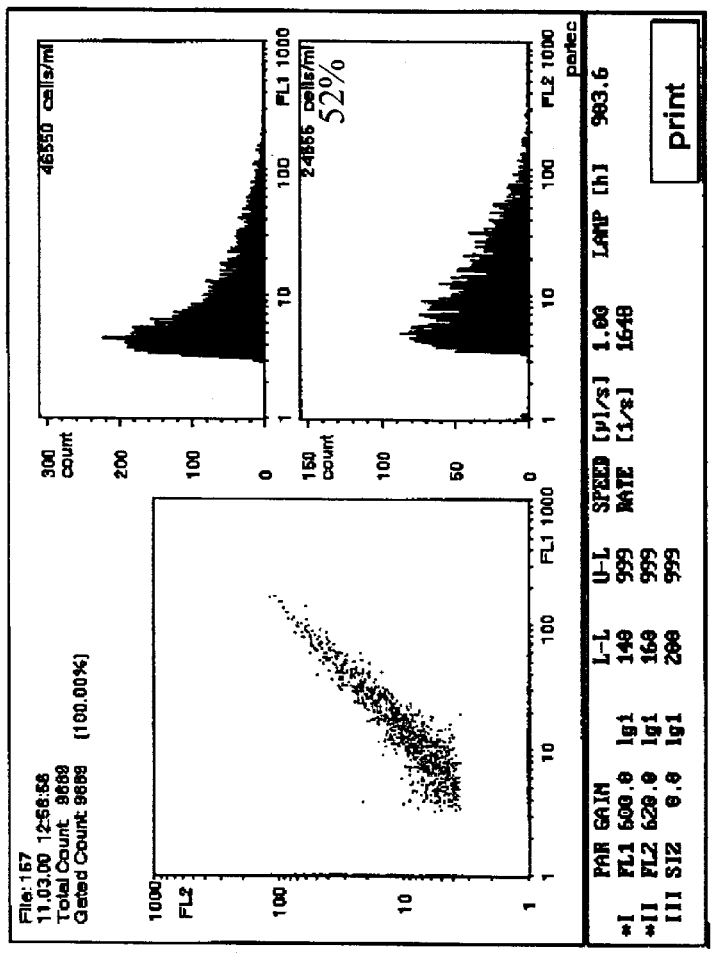
FIG. 6 shows platelets stored for three days without pentose (a) total platelets and (b) platelets activated with thrombin.
Figure 7:
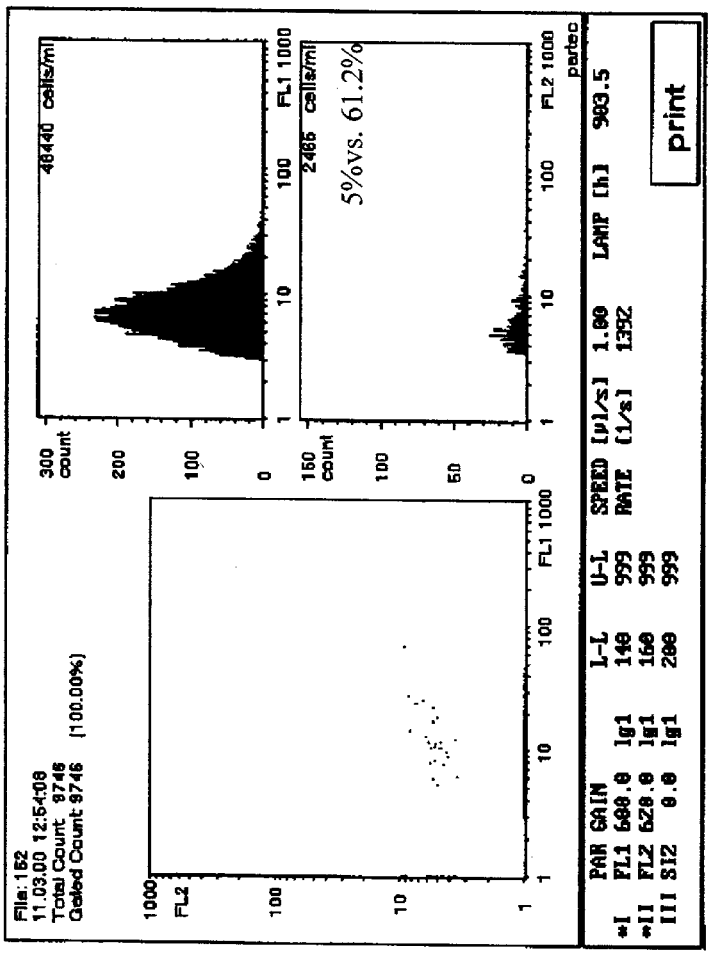
FIG. 7 shows basal P-selectin expression after three days with ribose.
Figure 8:
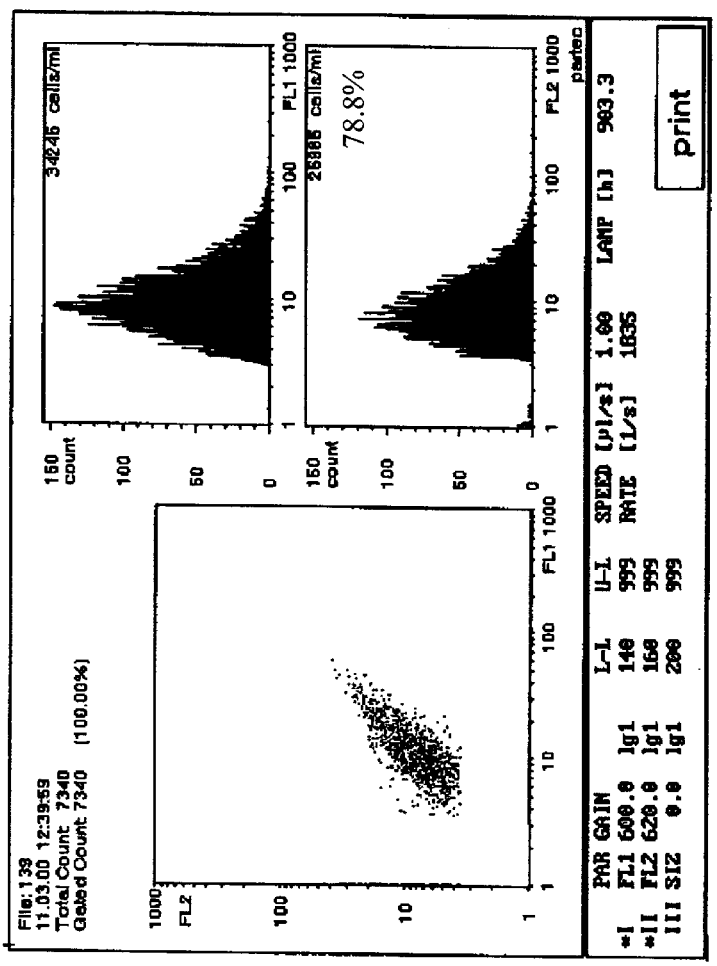
FIG. 8 shows P-selectin expression stored for three days with ribose after thrombin activation.

After three days storage under standard conditions, 61.2% of the platelets had been activated, that is, were essentially nonfunctional, as can be seen in FIG. 5. When a separate aliquot was challenged with thrombin, no additional activation was seen. In contrast, the cells stored with 153 nM D-Ribose showed only 5% positive (activated) cells and activation with thrombin showed retention of 78.8% activation activity even after three days of storage.

Longer term study showed that platelets stored with 150 nM D-Ribose retained activity of greater than 75% even at 8 days of storage and greater than 50% activity at 10 days of storage.

5. ATP Secretion

Figure 9:
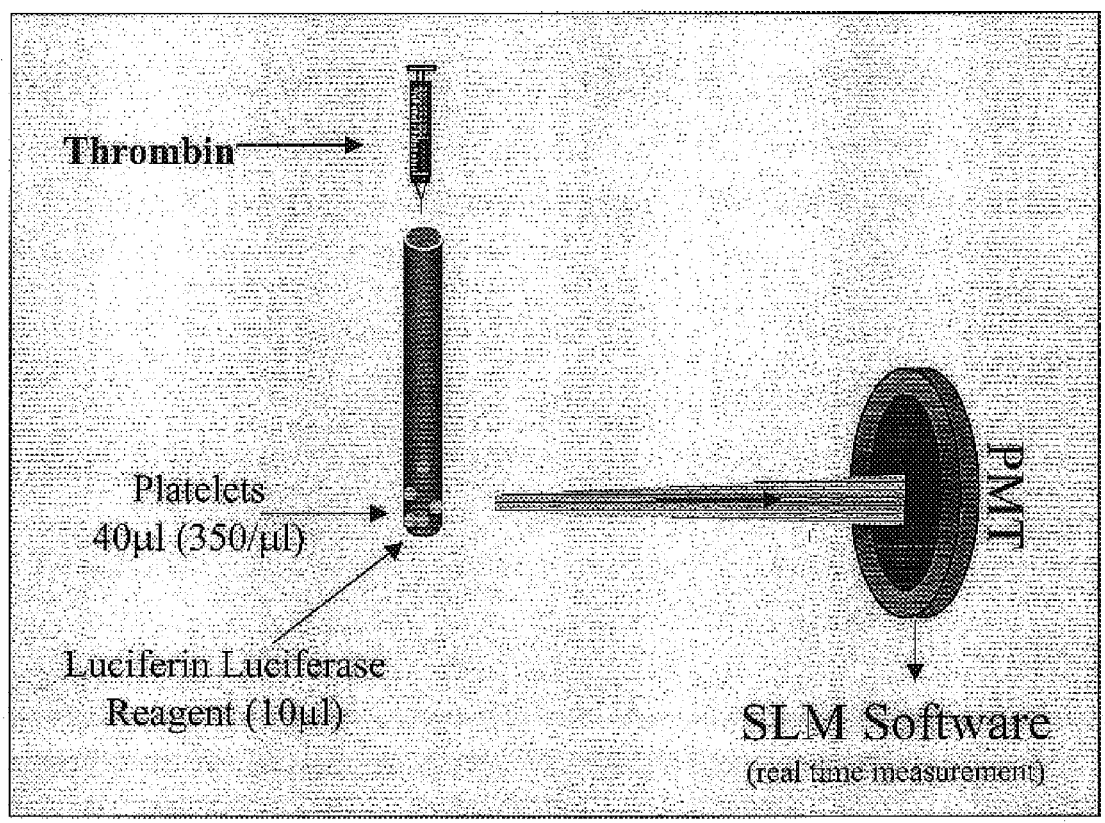
FIG. 9 is a schematic representation of the luciferin/luciferase assay.

The platelet dense granules shown in FIG. 1 contain ATP which is released in response to platelet agonists such as thrombin, collagen or adenosine diphosphate (ADP). The release reaction of ATP from platelets serves as another method to monitor platelet function. There are many methods to analyze ATP. A convenient method is the well known luciferin/luciferase reaction (Sigma Chemical, St. Louis). This assay is derived from the light producing system of the firefly. The substrate luciferin, in the presence of ATP, is cleaved by the enzyme luciferase, accompanied by the emission of light. The emitted light is measured by a photomultiplier tube Platelet suspensions containing about 350 units in 4 $\mu$l were mixed with 10 $\mu$l luciferin/luciferase reagent. An agonist is injected. As the platelet dense granules release ATP, the bioluminescent reaction occurs, which is measured by the photomultiplier tube. FIG. 9 shows a diagram of the reaction and measurement setup. The rate of reaction is recorded and as platelet function decays, the rate decays. Total ATP was measured by lysing the cells with Triton and determining ATP content. The results as presented in Table III are expressed as intact rate of ATP secretion.

TABLE III

ATP secretion in response to 10 nM thrombin:
Control vs. 150 nM D-Ribose Treated Platelets

| Sample | Day | Rate | Total ATP |
| --- | --- | --- | --- |
| Untreated | 1 | 1.9 | 3.1 |
| Ribose | 1 | 1.9 | 3.0 |
| Untreated | 3 | 0.76 | 1.2 |
| Ribose | 3 | 1.9 | 3.2 |
| Untreated | 5 | 0.28 | 0.72 |
| Ribose | 5 | 1.7 | 3.4 |
| Untreated | 7 | 0.00 | 0.00 |
| Ribose | 7 | 1.6 | 3.4 |

The results in Table III show that ATP secretion data of platelets treated with D-Ribose compared to platelets untreated show a profound effect not found with any other preserving agent. Control platelets were seen to lose activity during every day of storage and by day five mean the mean rate was less than 15%, while total ATP was less than 25% of baseline. For platelets treated with optimal amounts of D-Ribose the mean activity at five days was still at 90% of baseline, while day 7 activity was still in excess of 80%. The ATP secretion is dose dependent. 15 mM has no effect (and it was seen that this dose is toxic to platelets) and after 8 consecutive serial dilutions, the concentration was 1.5 nM and no preservative effect is seen. Therefore, this test was done at a concentration of 150 nM D-Ribose. It should be noted that the total ATP content of the treated cells actually rose by more than 10%.

6. Platelet Aggregation

As a second measure of the effect of ribose on platelets, platelet aggregation was estimated. Platelet aggregation is a crucial function of platelet activity; platelets that cannot aggregate are essentially nonfunctional. Platelets were stored as above.

The optical density of the suspension was measured before and after thrombin challenge. In this test, platelets stored in 1.5 mM or 150 pM D-Ribose showed no aggregation on challenge, while 15 $\mu$M D-Ribose showed a very weak effect. Platelets stored in 150 nM D-Ribose showed strong aggregation on challenge with thrombin.

Platelet aggregation was measured with a platelet aggregometer (Chronolog, Inc., Irvine, Calif.). Platelet-rich, turbid suspensions were stirred in a cuvette and the transmittance of light through the sample relative to a platelet poor blank is recorded. When a aggregating agent is added, activated platelets with exposed fibrinogen receptors (GPIIbIIIa) are brought in close contact with each other in a medium containing calcium and fibrinogen and form increasingly large platelet aggregates, accompanied by a decrease in turbidity. The change in optical density was then translated by the instrument to percent aggregation. Simple stated, as platelets clump, more light passes through the cuvette.

Platelet aggregation at day three in response to 10 nM thrombin with control platelets showed only one in five has an aggressive aggregation response, while all five of the D-Ribose treated platelet samples, displayed an aggressive response at day 3. At day five, four out of five D-Ribose platelet samples responded, and at day seven, three out of five D-Ribose platelet samples were able to aggregate in response to thrombin challenge.

7. pH

The pH of the platelet concentrates was monitored daily. Standard transfusion lore dictates that once the pH drops below 6.4, the platelets are discarded. The addition of D-Ribose may increase lactate production which would cause a drop in pH. Samples treated with D-Ribose at high levels (15 mM) typically show a drop to pH 6.0 by four days of storage. However at the preferred concentration of about 150 nM, although lactate is increased, the pH remains constant.

8. Other Pentoses

It is known that other pentoses may have similar effects as D-Ribose, either through intracellular conversion to ribose or a direct effect. Ribulose-5-phosphate, xylulose-5-phosphate and xylitol were tested for preservation of activity in stored platelets according to the methods of examples 1 to 6.

(A) Ribulose-5-phosphate:

Ribulose-5-phosphate was purchased from Sigma Chemical (St. Louis) and added to the standard CPD platelet storage solution. The following parameters of function were tested: ATP secretion in response to 10 nM thrombin; platelet aggregation; P-selectin expression in response to thrombin challenge; pH change; and platelet count. Platelet concentrate bags were obtained from a transfusion center within hours of collection. Aliquots were sampled from the platelet bags and concentrations of ribulose-5-phosphate were added for a final concentration from 1.5 mM down to 150 pM. Controls without ribulose-5-phosphate were analyzed for comparison. Samples were analyzed every 24 hours for platelet function. No difference from controls was observed for any of the above measured parameters.

(B) Xylulose-5-phosphate

Xylulose-5-phosphate was purchased from Sigma and added to the CPD platelet storage solution. The experimental procedure was carried out per example 8(A). It was found that platelets stored with xylulose-5-phosphate, measured as ATP secretion showed retention of 64.5% of the basal value at five days. Platelet aggregation was weak at five days, while the control platelets failed to aggregate. P-selectin spontaneous expression of the five-day xylulose-5-phosphate treated platelets was 37.5% versus 64.1% for the control platelets. In response to 10 nM thrombin challenge, the P-selectin expression increased to 67.7%.

(C) Xylitol

Surprisingly, the pentose-related alcohol xylitol showed some benefit for the preservation of platelet function. However, the trends were inconsistent and concise conclusions would not be made.

9. Reduction of Bacterial Contamination

It was surprisingly found that addition of D-Ribose to the storage cocktail resulted in lower incidence of bacterial contamination. Bacterial contamination was measured by colony counts in standard Petri dishes that had been inculated with the test solution. It is assumed that the millimolar glucose concentration in most platelet storage solutions contributes to the growth of bacteria. As noted above, Murphy (Table II) discloses a glucose-free solution for the storage of platelets. Elimination of reduction of glucose levels from millimolar to micromolar concentrations has a profound effect in reducing bacterial contamination, however, platelet function at five days, as measured by ATP secretion and P-selectin expression, was poor. It was found that glucose could be eliminated or reduced to micromolar concentration in the storage solution if D-Ribose at the preferred concentration of 150 nM was added to the solution, while platelet function was similar to that found in examples 1 to 6 above, performed on platelets stored in the presence of glucose.

10. Mechanism of D-Ribose Preservation of Platelet Function,

None of the standard mechanisms proposed for ribose enhancement of physiological function by the production of ATP seems operative in platelet preservation. The very low optimal dosage in the nanomolar range would seem to be insignificant for energy production. Platelets have very high metabolic rates, especially as they are stored at room temperature. They contain high levels of glycogen, an energy source for anaerobic glycolysis; and mitochondria which can carry out oxidative phosphorylation. It has been noted that platelets require oxygen for best survival, possibly because glycolysis results in lactate production. Nevertheless, this invention clearly shows that D-Ribose is a preservative agent for platelet preservation.

This invention has been described in terms of certain embodiments. Following the teachings of this application, those skilled in the art can easily make substitutions and modifications to the embodiments without departing from the spirit and scope of the invention. Therefore, such substitutions and modifications are within the scope of the appended claims. All references cited within are hereby incorporated by reference.

We claim:

1. A platelet storage medium comprising an isotonic, balanced salt solution and of a pentose at a concentration of about 100 nanomolar to 1.5 millimolar.

2. The medium of claim 1 wherein the pentose is D-Ribose, xylitol-5-phosphate or xylitol.

3. The medium of claim 1 wherein the pentose is present at a concentration of about 50 nanomolar to 15 micromolar.

4. The medium of claim 1 wherein the pentose is present at a concentration of about 100 nanomolar to five micromolar.

5. The medium of claim 1 further comprising a magnesium salt present at a concentration of 0.5 to 2.5 millimolar.

6. The medium of claim 1 from which glucose has been excluded.

7. The medium of claim 1 wherein the balanced salt solution is blood plasma.

8. A method of storing platelets comprising (a) the separating of platelets from whole blood or plasma; (b) suspending the platelets in balanced salt solution or plasma at a concentration of about $5 \times 10^5$ to about $10 \times 10^{10}$ platelets per millimeter and (c) adding the platelet suspension to a collection bag comprising pentose in an amount sufficient to form a concentration of from about 50 nanomolar to about 15 micromolar when the platelet suspension is added.

* * * * *